(12) United States Patent
Johnson

(10) Patent No.: US 6,571,605 B2
(45) Date of Patent: Jun. 3, 2003

(54) CONSTANT-HEAD SOIL PERMEAMETER FOR DETERMINING THE HYDRAULIC CONDUCTIVITY OF EARTHEN MATERIALS

(76) Inventor: Larry Keith Johnson, 4424 Middle Ridge Dr., Fairfax, VA (US) 22033

(\*) Notice: Subject to any disclaimer, the term of this patent is extended or adjusted under 35 U.S.C. 154(b) by 0 days.

(21) Appl. No.: 09/764,375

(22) Filed: Jan. 19, 2001

(65) Prior Publication Data

US 2002/0095984 A1 Jul. 25, 2002

(51) Int. Cl.$^7$ .................. G01N 15/08; G01N 15/02; G01F 23/08; G01F 23/58
(52) U.S. Cl. ................ 73/38; 73/861.46; 73/152.05
(58) Field of Search .................... 73/38, 37, 152.05, 73/861.46

(56) References Cited

U.S. PATENT DOCUMENTS

| | | | |
|---|---|---|---|
| 3,892,126 A | 7/1975 | Curtin | 73/38 |
| 3,926,143 A | 12/1975 | Hothan | 116/118 R |
| 3,945,247 A | 3/1976 | Anderson | 73/73 |
| 4,072,044 A | 2/1978 | Farwell et al. | 73/38 |
| 4,099,406 A | 7/1978 | Fulkerson | 73/73 |
| 4,182,157 A | 1/1980 | Fink | 73/38 |
| 4,341,110 A | 7/1982 | Block | 73/38 |
| 4,561,290 A | 12/1985 | Jewell | 73/38 |
| 4,829,817 A * | 5/1989 | Kozlowski | 73/155 |
| 4,884,436 A * | 12/1989 | Ankeny et al. | 73/38 |
| 4,956,993 A | 9/1990 | Mehler | 73/38 |
| 4,969,111 A | 11/1990 | Merva | 364/556 |
| 4,984,447 A | 1/1991 | Phillips | 73/38 |
| 5,050,493 A * | 9/1991 | Prizio et al. | 100/106 |
| 5,157,959 A | 10/1992 | Ankeny et al. | 73/38 |
| 5,161,407 A * | 11/1992 | Ankeny et al. | 73/38 |
| 5,219,388 A * | 6/1993 | Meletiou et al. | 73/155 |
| 5,345,820 A * | 9/1994 | Bernhardt | 73/155 |
| 5,520,248 A | 5/1996 | Sisson et al. | 166/250.02 |
| 6,178,808 B1 * | 1/2001 | Wang et al. | 73/38 |
| 6,212,941 B1 * | 4/2001 | Cholet | 73/38 |
| 5,804,715 A * | 9/1998 | Bennett | 73/170.32 |
| 5,861,750 A * | 1/1999 | Anderson et al. | 324/347 |
| 6,098,448 A * | 8/2000 | Lowry et al. | 73/38 |
| 6,105,418 A | 8/2000 | Kring | 73/38 |

OTHER PUBLICATIONS

A. Amoozegar, "A Compact Constant–Head Permeameter for Measuring Saturated Hydraulic Conductivity of the Vadose Zone", *Soil Science Society of America Journal*, vol. 53, No. 5, Sep.–Oct. 1989, pp. 1356–1361.*
A. Amoozegar, "Comparison of the Glover Solution with the Simultaneous–Equations Approach for Measuring Hydraulic Conductivity", *Soil Science Society of America Journal*, vol. 53, No. 5, pp. 1362–1367, Sep.–Oct. 1989.*
R. E. Glover/Carl N. Zangar, Theory and Problems of Water Percolation, Bur. Relm., Dnvr. C. 1953.

(List continued on next page.)

*Primary Examiner*—Helen Kwok
*Assistant Examiner*—David J. Wiggins
(74) *Attorney, Agent, or Firm*—Marion P. Lelong

(57) ABSTRACT

A constant-head soil permeameter for determining hydraulic conductivity of earthen materials is inserted into a borehole at the desired test depth. A calibrated reservoir, disposed on the ground surface, is attached thereto with a suitable length of hose. Water is added to the calibrated reservoir and allowed to flow freely into the borehole until an equilibrium level is reached in the borehole and inside the soil permeameter. The water flowing to the permeameter is throttled by buoyant float pressure that is greatly increased by a lever-and-link valve control assembly which provides considerable mechanical advantage, thereby allowing better constant head control and much greater depths of testing than previously attained by known permeameters. A filtered vent system, backflow check valve, and seals restrict entry of soil particles and debris, thereby minimizing cleaning and maintenance of the invention. The soil permeability is determined by solving appropriate mathematical equations which utilize the equilibrium height of water, rate of water flow, and dimensions of the borehole as input parameters.

18 Claims, 10 Drawing Sheets

OTHER PUBLICATIONS

R. Allan Freeze, J. A. Cherry, Groundwater, Prentice–Hall, Inc., Enalw. Cliffs, NJ., 1979 pp 15–77.

W. D. Reynolds, E. D. Elrich, A Reexamination of the Constant–Head Well Perm. Mthod. for Meas. Sat. Hud. Cond. above the WT, Soil Sci, 1983, p 250–268.

A. Amoozegar, A. W. Warrick, Hydraulic Conductivity of Saturated Soils: Field Methods, Soil Science Soc AM, Madison, Wi., 1986, pp 735–770.

W. D. Reynolds, D. E. Elrich, Laboratory and Numerical Assessment of the Guelph Permeameter Method, Soil Science, vol. 144, pp 282–289, 1987.

A. Amoozegar, A Constant Head, (compact) Permeameter . . . , Comparison of the Glover Solution . . . , Soil Sci. AM, vol. 53, 1989, pp 1356–1367.

* cited by examiner

CONSTANT-HEAD SOIL PERMEAMETER FOR DETERMINING THE HYDRAULIC CONDUCTIVITY OF EARTHEN MATERIALS

BACKGROUND OF THE INVENTION

1. Field of the Invention

This invention relates to the hydraulic conductivities of liquids through permeable materials and particularly relates to the conductivity of water through earth. It also relates to testing such conductivity from the surface of the earth to great depths beneath the surface and above the water table while preventing contamination by falling soil and debris. It more particularly relates to instruments that establish a static head of water within a borehole and maintain the water at this predetermined level by use of a float and valve system. It specifically relates to a float and valve system that provides a mechanical advantage ratio enabling use at such great depths.

2. Review of the Prior Art

It is often important to estimate the hydraulic conductivities of earthen materials in order to safely and economically develop lands for urban and agricultural uses. Hydraulic conductivity values are important considerations in design and construction of building and roadway foundations, on site sewage wastewater treatment systems, and storm water infiltration facilities. These values are important for artificial treatment of wetlands, and for estimating the rate of transport of liquid contaminants from waste disposal sites and leaking storage tanks. Hydraulic conductivity values are additionally important in design of irrigation systems and drainage of agricultural lands.

Soil hydraulic conductivity can be used to describe the ability of earthen materials to transmit water. Darcy's Law describes the relationship of the volume of water, moving through a cross sectional area of soil (commonly known as flux) along the hydraulic gradient of the water flow path, to the hydraulic conductivity. Under saturated conditions, such as below a water table, hydraulic conductivity is referred to as saturated hydraulic conductivity. Even though Darcy's law was originally developed to describe saturated flow, the principles of the law can be applied to water movement in partially saturated soils above the water table.

The determination of hydraulic conductivity under field conditions can be complicated because of the natural variation of soil properties and the specific need for which the test is being conducted. Soils typically contain multiple contrasting layers and often exhibit significantly differing hydraulic conductivity values along preferential flow paths within the soil matrix.

Prior art instruments developed for measuring hydraulic conductivity of soils above the water table in the field have generally fallen into three groups. The first group introduces either a ponded static (i.e., constant) or a variable (i.e., falling) head of water into the bottom of an unlined borehole below the ground surface or into a confining ring in contact with the ground surface. Instruments that establish a static head of water within a borehole maintain the water at a predetermined level, usually by use of either a float and valve system or a marriott tube system. The rate of water flow necessary to maintain a constant water level in the borehole at the predetermined level is utilized to estimate hydraulic conductivity of the soil. Methods used to measure the saturated hydraulic conductivity in a borehole utilizing a constant head of water have been referred to as the shallow well pump-in technique or constant-head well permeameter. Instruments in this first group that utilize a falling head procedure usually measure the drop of water from a predetermined level in a lined or unlined borehole as it dissipates into the soil to estimate hydraulic conductivity.

The second group of instruments applies water through a semi-permeable membrane to a soil surface, which is under negative pressure (tension), to measure unsaturated hydraulic conductivity. The third group of instruments utilizes various methodologies, which include electrical resistivity procedures and gas or liquid injection into the soil through penetrating probes. The instruments in the third group typically require a power source, fluid or gas pumps, multiple chambers, borehole packers, electronic data loggers, and complex analysis procedures.

U.S. Pat. No. 6,105,418 discloses a constant-head float valve assembly which includes a J-shaped fluid conduit for intermittently delivering water from a supply container to a borehole. As the float moves downward with dissipating water levels, a shutoff valve is contacted and thereby opened to replenish the water in the borehole. The rising water moves the float upward and away from the valve, thereby allowing pressure of the incoming water to close the valve again.

U.S. Pat. No. 4,561,290 utilizes a float valve assembly, connected to a water supply reservoir, to regulate water inflow and obtain a constant water level within a borehole. The float responds to a rising water level by regulating water flow through a valve and thereby maintaining a constant water level.

However, neither of these devices incorporates an apparatus for magnifying the vertical force of the float body that is necessary for valve regulation at large depths and flow volumes, nor do they incorporate a backflow check valve to prevent incident entry of suspended soil particles and other contaminates into the float chamber. In addition, neither of these devices includes a means for eliminating the entry of contaminants through its air equalizing passage into the interior of the device.

Soil hydraulic conductivity has been historically measured on a smaller scale in the laboratory, utilizing a falling or constant head of water applied to soil core samples retrieved from the field or on remolded soil samples. Laboratory centrifugal force methods are also utilized to estimate hydraulic conductivity. Laboratory measurements are often significantly at variance with in situ field measurements because of the differing methodologies and the inherent difficulty of obtaining undisturbed soil samples and replicating natural environmental and stress conditions in the laboratory.

It is desirable to have the capability to conduct hydraulic conductivity tests at any depth in earthen materials above the permanent water table. Such depths may range from zero to many meters below the ground surface. In addition, it is desirable to have adequate flow capacity for maintaining flow equilibrium in a wide range of soils. Clay soils often have slow permeability, whereas sandy or gravelly soils often have high permeability and, therefore, a greater equilibrium flow rate.

Prior art inventions that utilize a float system alone do not provide a mechanical advantage ratio, thereby limiting testing to relatively shallow depths. Inventions utilizing the marriott tube principle to establish a constant water level are also limited to relatively shallow depths of testing.

A buoyant force is provided by a float in accordance with Archimedes's Principle which states that the buoyant force on a body immersed in a fluid is equal to the weight of the fluid displaced by that body. The displacement volume of any float of practical geometric shape that can fit in a small-diameter borehole is relatively small, therefore the depth at which such float can provide throttling of a valve by direct buoyant force alone is limited to relatively shallow depths and small flow rates. There is accordingly a need for an apparatus that is sufficiently rugged and versatile to measure hydraulic conductivities of soils inside a borehole at a variety of depths above the water table, ranging from shallow to deep. There is also a need for a device that can be used inside a borehole, wherein the device is subject to being struck by falling soil particles and debris, without contamination by such particles and debris through the air vent hole at its top or through water outlets at its bottom.

SUMMARY OF THE INVENTION

It is an object of the invention to provide a simple and sturdy apparatus which functions as a constant-head soil permeameter for estimating saturated hydraulic conductivity of in situ earthen materials above the water table by establishing a constant head of water at a predetermined level in a borehole that is dug below the ground surface with ordinary hand auger equipment or with power equipment.

It is a further object to provide a soil permeameter that can, without incorporation of electronics, be effectively used to estimate hydraulic conductivity at desired test depths normally encountered above the water table and at depths much greater than the depths at which known devices that utilize a float system can be employed.

It is an additional object to provide a constant-head soil permeameter that can be effectively used to determine hydraulic conductivity within a wide range of soil permeability.

It is also an object to provide a soil permeameter that avoids malfunction in the field by minimizing contamination from soil particles and debris falling from the side of the borehole.

In accordance with these objects and the principles of the invention, the soil permeameter of this invention is an apparatus which incorporates a float and a mechanical linkage system that greatly increases the forces applied by the float to throttle water flow at the control valve.

The constant-head soil permeameter of this invention seeks to overcome disadvantages of other float systems by greatly increasing the buoyant force resulting from submergence of a float alone. The permeameter increases the buoyant force by use of a compound lever and link assembly, as a part of its float system, which provides a mechanical advantage ratio ranging from approximately 10:1 at full valve opening to approximately 60:1 at full valve closure. The resultant available maximum throttling force is, therefore, approximately 60 times greater than simple buoyant force at full valve closure. The effective testing depth range of the permeameter is from 15 centimeters to about 30 meters. The permeability testing range of the apparatus is from $10^{-6}$ centimeters/second to $10^{-2}$ centimeters/second. The range of water flow volume through the apparatus is from zero to 2000 milliliters/minute or more at depths greater than one meter.

This constant-head soil permeameter comprises a tubular cylinder having a top end, a bottom end, means for introducing a liquid into the top end, means for selectively closing the bottom end, and means for preventing falling debris and soil from entering the top end while enabling air to flow into and out of the cylinder, the top end and the bottom end being defined in relation to usage within a vertically disposed borehole in materials permeable to the liquid. The cylinder contains a float system that provides a mechanical advantage ratio for shutting off the introduction of liquid.

This float system comprises a compound lever and link assembly that functions as a valve control assembly and is hereinafter thus identified. It is particularly operative when:
A) the liquid is water, the materials are earthen, and the borehole has a bottom disposed above a water table in the earthen materials; and
B) the mechanical advantage ratio ranges from approximately 10:1 at full valve opening to approximately 60:1 at full valve closure.

The valve control assembly, described hereinafter with water as the liquid, comprises the following lever and link assembly:
A) a valve support bracket which is longitudinally disposed and rigidly supported within the cylinder, adjacent to the inner side thereof;
B) an actuating lever arm, having two ends, which is attached at one end to a first pivot which is attached to the valve support bracket;
C) a link, having two ends, which is attached at its lower end to a second pivot which is attached to but spaced apart by a selected distance from the first pivot; and
D) a valve seat retaining lever arm, having two ends, which is pivotally attached at one end to the valve support bracket and is pivotally attached at its other end to a pivot attached to the upper end of the link.

The top end of the cylinder comprises a top stopper, having an upper side and a lower side, which is rigidly attached to the cylinder and is encircled by an o-ring in sealing contact with the cylinder. The means for introducing water into the top end of the cylinder comprises a reservoir for containing water, a hose connection which is rigidly attached to the top stopper and projects outwardly from its upper side and has a bore therewithin, a hose for connecting the reservoir to the hose connection, and a valve body which is rigidly attached to the lower side of the stopper and has a bore therewithin in fluid communication with the bore within the hose connection.

The valve seat retaining lever arm comprises a valve seat which is attached thereto in facing relationship to the valve body and is adapted for selectively shutting off the introducing of water from the reservoir.

The cylinder additionally contains a buoyant float body that is axially movable within the cylinder and has upper and lower surfaces. The upper surface exerts pressure against the other end of the actuating lever arm when the float is supported by water within the cylinder.

The constant-head soil permeameter may be described as comprising the following lever and link assembly which provides a mechanical advantage ratio:
A) a valve support bracket having an upper pair and a lower pair of spaced-apart lugs attached perpendicularly thereto and projecting toward the center of the cylinder;
B) an actuating lever arm having one pair of spaced-apart lugs attached perpendicularly thereto at its pivot end and projecting upwardly, being attached to the lower pair by the first pivot;
C) a link having two pairs of the spaced-apart lugs attached perpendicularly thereto at the upper and lower ends thereof and projecting toward the valve support bracket, one pair being attached by the second pivot to the one pair of spaced-apart lugs on the pivot end of the actuating lever arm and being spaced from the first pivot by a selected distance; and D) a valve seat retaining lever arm having two pairs of spaced-apart lugs attached perpendicularly thereto at the ends thereof and projecting in opposite directions, one pair being pivotally attached to the upper pair on the valve support bracket and the other pair being pivotally attached to the pair of spaced-apart lugs on the upper end of the link.

The means for preventing falling debris and soil from entering the top end of the cylinder while enabling air to flow into and out of the cylinder comprises an inverted J-shaped tube, having a long portion which passes through the stopper and a short portion having a filter screen at its outer end, the filter screen being disposed to face toward the upper side of the stopper and being spaced from the upper side.

The means for selectively closing the bottom end of the cylinder comprises a bottom stopper, having an upper surface and a lower surface, which is rigidly attached to the cylinder, an o-ring encircling the stopper and in sealing contact with the cylinder, an axially disposed bolt attached to the stopper and extending upwardly beyond its upper surface, at least one longitudinally disposed hole extending through the bottom stopper, and a check valve disposed beneath the lower surface, whereby reverse flow of water from the borehole toward the stopper lifts the check valve and closes the hole and the bottom end.

This constant-head soil permeameter, adapted for operational use within a borehole in earthen materials, comprises a cylindrical housing having a top end and a bottom end which has a flow-through means for allowing water entering the top end to form a first water level within the housing and then to flow through the bottom end into the borehole to form a second water level therewithin when the second water level is lower than the first water level and having a closing means for preventing water from flowing into the cylindrical housing when the second water level is higher than the first water level.

This flow-through means comprises a bottom stopper which is rigidly attached to the cylindrical housing, has a countersunk bottom surface forming a downwardly extending skirt that contacts the bottom of the borehole when the permeameter is resting thereupon, has at least one longitudinally disposed hole through the stopper, and has at least one laterally extending hole through the skirt.

This closing means comprises a check valve guide which is axially and rigidly attached to the countersunk bottom surface of the stopper, a disk-shaped check valve which is loosely and axially fitted to the check valve guide, and a disk-shaped baffle, having a plurality of longitudinally disposed holes therethrough, which is rigidly and perpendicularly attached to the check valve guide and disposed beneath the check valve, whereby backflow of water from the borehole toward the bottom stopper passes through the plurality of holes in the baffle and lifts the check valve to block the at least one longitudinally disposed hole in the bottom stopper.

The rate of water flow into the borehole that is necessary to maintain the constant head is recorded at appropriate intervals during the test period. The information recorded during the test, which also includes height of constant water column, rate of flow, and borehole geometry, is factored into an appropriate mathematical equation to provide an estimate of hydraulic conductivity.

DETAILED DESCRIPTION OF THE PREFERRED EMBODIMENTS

Figure 1:
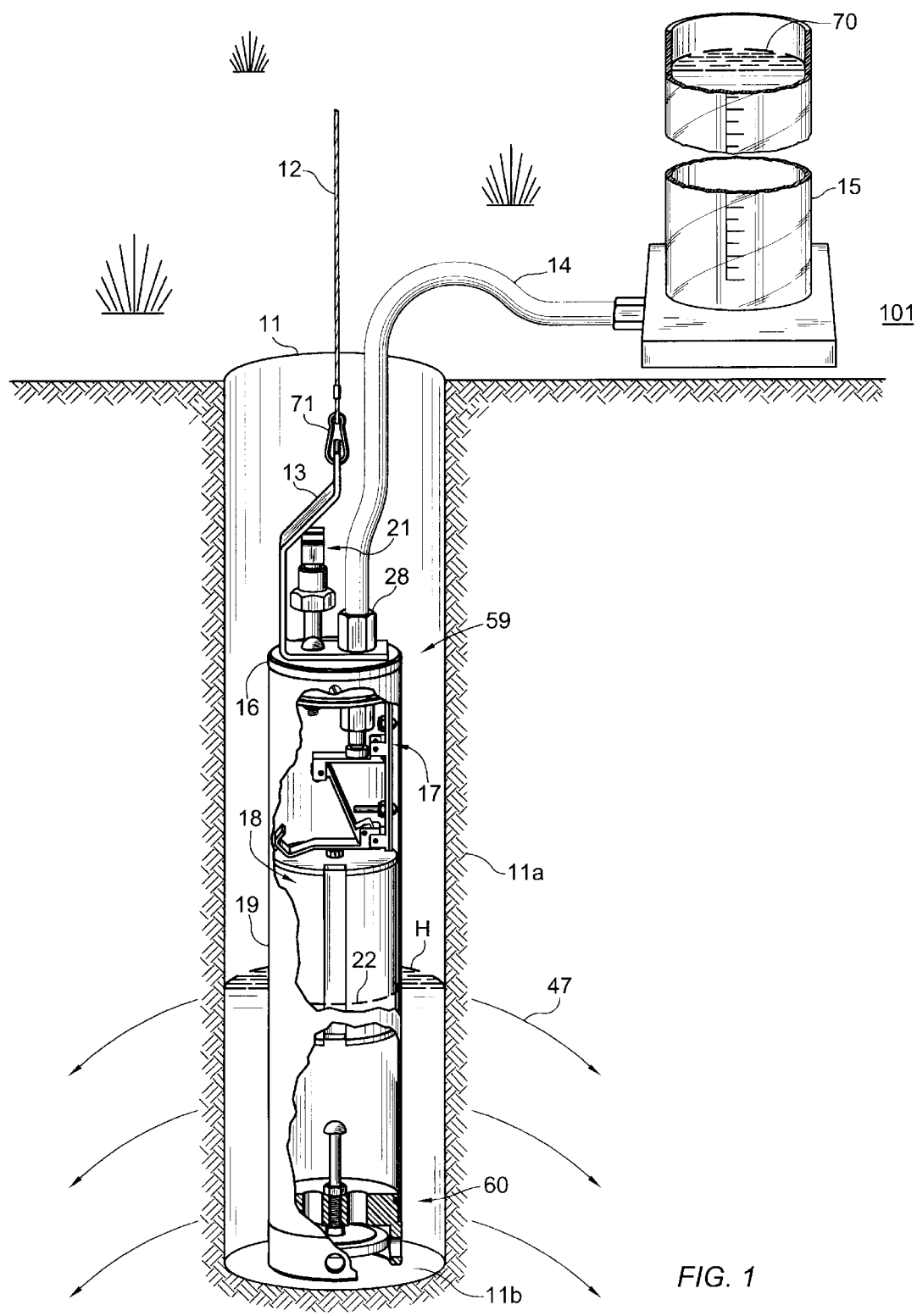
FIG. 1 is an isometric and partial cutout view of the soil permeameter in place in a borehole dug in earthen materials.

As shown in FIG. 1, the constant-head soil permeameter of this invention comprises calibrated reservoir 15 which is disposed on ground surface 101 near borehole 11, cylindrical housing 19 which is lowered into borehole 11, lifting and/or support means for housing 19, means for water delivery from reservoir 15 to housing 19, means for venting air from housing 19, means for providing a mechanical advantage ratio for shutting off water flow into housing 19, and means for preventing debris and fallen earth particles from entering housing 19. Inside of housing 19 are valve control assembly 17, float assembly 18, base assembly 60, and portions of flow control assembly 59.

Figures 4A, 4B:
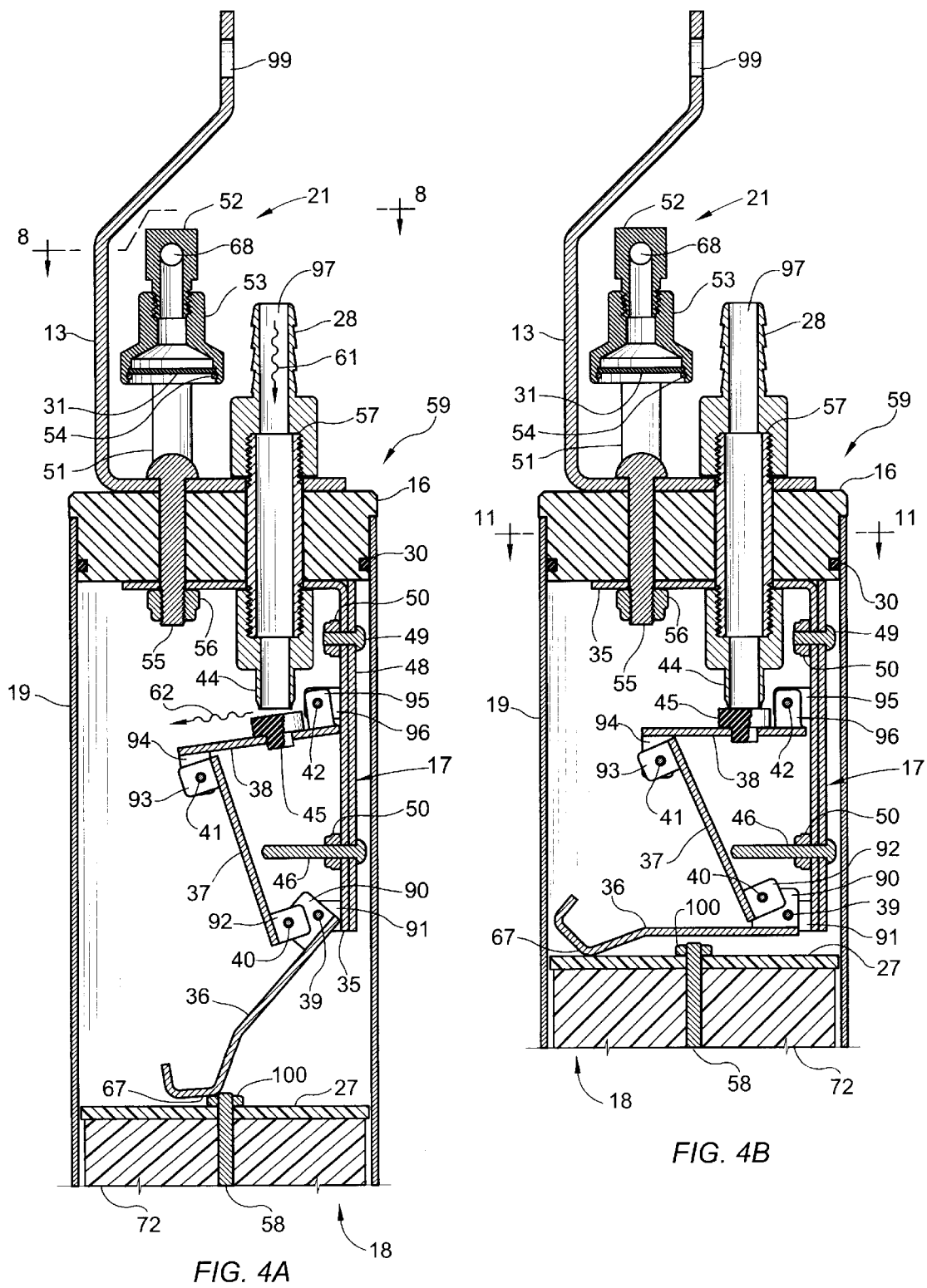
FIG. 4A is a sectional view of the upper part of the constant-head soil permeameter showing the top stopper, its o-ring, the filter vent assembly, the air vent assembly and the valve control assembly in its fully opened position.
FIG. 4B is a sectional view of the upper part of the constant-head soil permeameter showing the valve control assembly in its fully closed position, as in FIG. 2A.

Housing 19 consists of a tubular cylinder suitable for isolation and protection of interior components of the permeameter. The lifting and/or support means for suspension and stabilization of cylindrical housing 19 comprises cable 12, which is secured at its lower end through hole 99, as seen in FIGS. 4A, 4B of suspension bracket 13, at snap connection 71 and at its upper end to any suitable anchoring mechanism above ground surface 101. Hose connection 28 provides the entry port of water into housing 19 during tests. The means for water delivery from reservoir 15 to housing 19 comprises hose 14, which has a suitable length for the testing depth. The permeameter may rest on bottom 11b of borehole 11 or may be supported at any desired height above bottom 11b by cable 12.

Top stopper 16, as shown in FIGS. 2A, 3, 4A, and 4B, provides a rigid mounting base for valve control assembly 17, suspension bracket 13, filter vent assembly 21, and hose connection 28 as additional portions of flow control assembly 59. Top stopper 16 incorporates an o-ring 30 to provide a seal between stopper 16 and housing 19, thereby preventing soil particles and debris from entering the invention in the annular space between top stopper 16 and housing 19.

Figure 11:
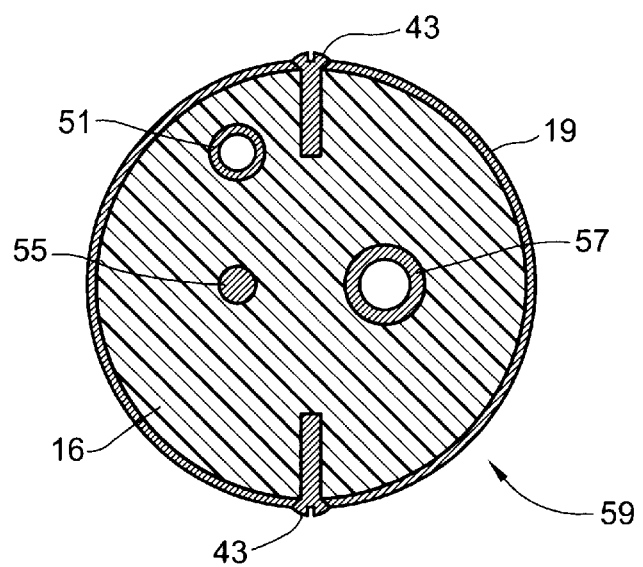
FIG. 11 is a sectional view of the top stopper, taken along line 11—11 in FIG. 4B, of the constant-head soil permeameter.

Hose connection 28 and valve body 44 are hydraulically connected and secured through top stopper 16 by commercial pipe 57, as shown in FIGS. 4A, 4B, and 11. Suspension bracket 13 and valve control assembly 17 are additionally secured to top stopper 16 by commercial bolt 55 and commercial nut 56. Top stopper 16 is secured to housing 19 by commercial machine screws 43, as seen in FIGS. 2A and 11.

Filter vent assembly 21, as shown in FIGS. 2A, 3, 4A, 4B, and 8, comprises commercial pipe nipple 51, commercial pipe elbows 52, filter housing 53, filter screen 31, and filter retaining snap ring 54. Pipe nipple 51 is threadably fastened to top stopper 16 in a manner that allows free movement of air through vent pathway 68 in filter vent assembly 21 and top stopper 16. Filter vent assembly 21 is constructed as an inverted J-shape to discourage entry of soil particles into the cylinder chamber through gravitational action while allowing free passage of atmospheric gas and excluding soil particles and other debris. Because filter screen 31 faces downwardly and is spaced from the upper side of stopper 16, there is substantially no opportunity for soil and debris to pass through screen 31 into vent pathway 68, whereby contamination of the apparatus is substantially impossible.

Figures 2A, 2B, 3:
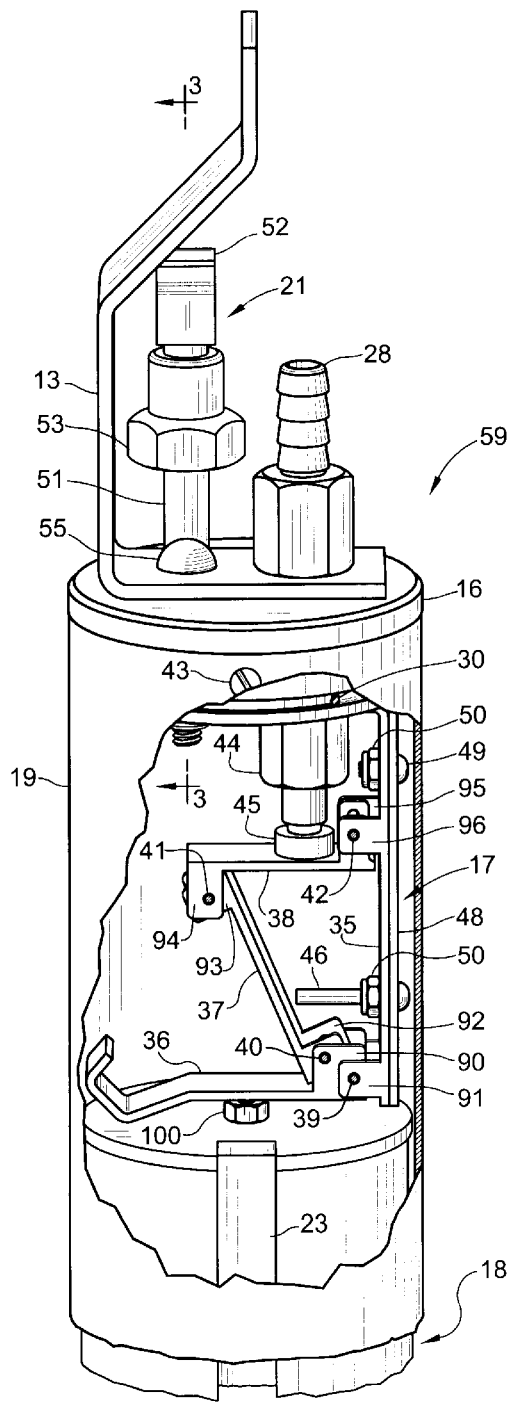
FIG. 2A is an isometric and partial cutout view of the upper part of the soil permeameter, showing the top stopper and the valve control assembly in its fully closed position.
FIG. 2B is an isometric and partial cutout view of the lower part of the constant-head soil permeameter, showing the base assembly and the check valve in its open position.
FIG. 3 is a sectional view of the upper part of the soil permeameter showing the top stopper, the filter vent assembly, and the air vent pathway, taken along line 3—3 in FIG. 2A.

Valve control assembly 17, as shown in FIGS. 2A, 4A, and 4B, comprises valve body 44, valve seat 45, valve seat retaining lever arm 38, valve support bracket 35, stabilizing bracket 48, link 37, and actuating lever arm 36. Valve support bracket 35 and stabilizing bracket 48 are fastened together by commercial bolts 49 and 46 and by commercial nuts 50.

Valve support bracket 35, actuating lever arm 36, link 37, and valve seat retaining lever arm 38 comprise pairs of spaced apart and perpendicularly extending support lugs, shown in FIGS. 2A, 4A, and 4B. Each lug pair has at least one pivot which comprises a hole drilled completely through its lug pair and a pivot alignment pin inserted completely through each drilled hole of the lug pair, thereby serving as an axis of rotation. The pivot alignment pins are crimped on the outsides of the lugs to ensure retention. These pivot alignment pins are parallel to each other and provide a nearly frictionless connection between actuating lever 36, link 37, valve seat retaining lever arm 38, and stationary valve support bracket 35.

Each lug pair has at least one pivot, except for actuating lever arm 36 which comprises two pivots on its single lug pair. The pivots allow actuating lever arm 36, link 37, and valve seat retaining lever arm 38 to move freely in a plane parallel to the longitudinal axis of stationary valve support bracket 35.

Actuating lever arm 36, which comprises a single lug pair 90, rotates axially around pivot 39, which is also connected to lug pair 91 of valve support bracket 35. Valve retaining lever arm 38, which comprises two lug pairs 94 and 95 extending in opposite directions, rotates axially around pivot 42 which is also connected to lug pair 96 of valve support bracket 35. Link 37, which comprises two lug pairs 92 and 93 extending in opposite directions, is connected at pivot 40 to actuating lever arm 36 and at pivot 41 to valve retaining lever arm 38. Link 37 rotates axially around both pivots 40 and 41 in response to the rising and lowering of float assembly 18.

Valve support bracket 35 provides a rigid stationary connection between valve seat retaining lever arm 38 and actuating lever arm 36. Link 37 provides a movable rigid connection between valve seat retaining lever arm 38 and actuating lever arm 36. Valve control assembly 17 is shown in a fully opened position in FIG. 4A and in a fully closed position in FIGS. 2A and 4B.

Figure 6:
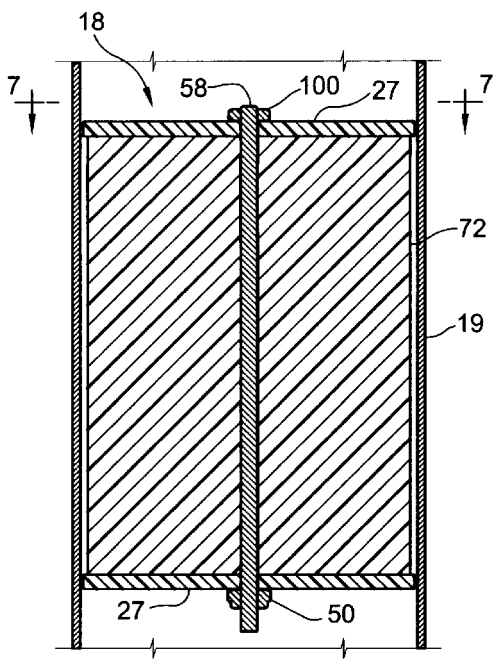
FIG. 6 is a sectional view of the buoyant float body and the surrounding housing of the constant-head soil permeameter.
Figure 7:
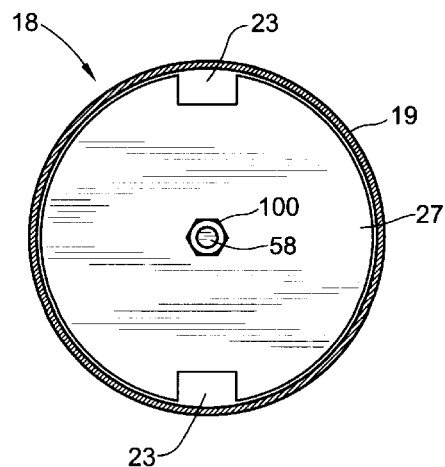
FIG. 7 is a plan view of the float assembly, taken along line 7—7 in FIG. 6, and a sectional view of the surrounding housing of the constant-head soil permeameter.
Figure 8:
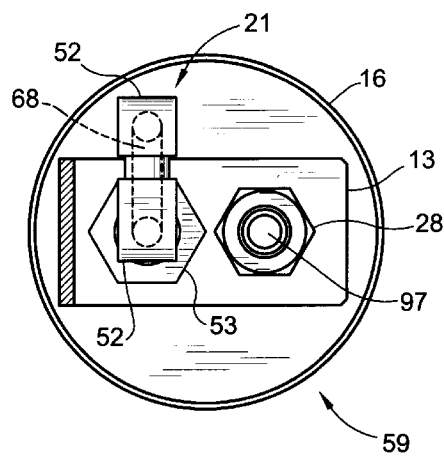
FIG. 8 is a plan view of the filter vent assembly and hose connection at the top end of the cylinder and a partial sectional view of the suspension bracket, taken along line 8—8 in FIG. 4A.
Figure 9:
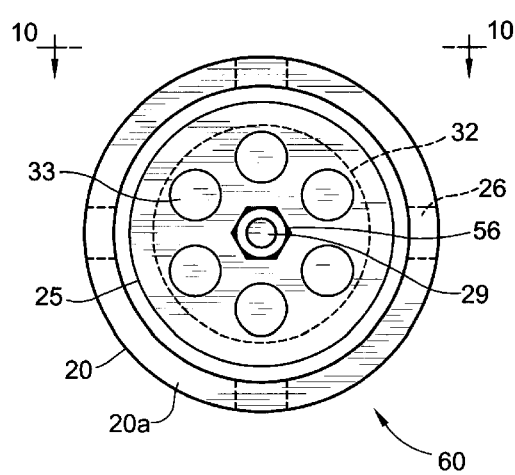
FIG. 9 is a bottom view of the base assembly, taken along line 9—9 in FIG. 5B, of the constant-head soil pemeameter.
Figure 10:
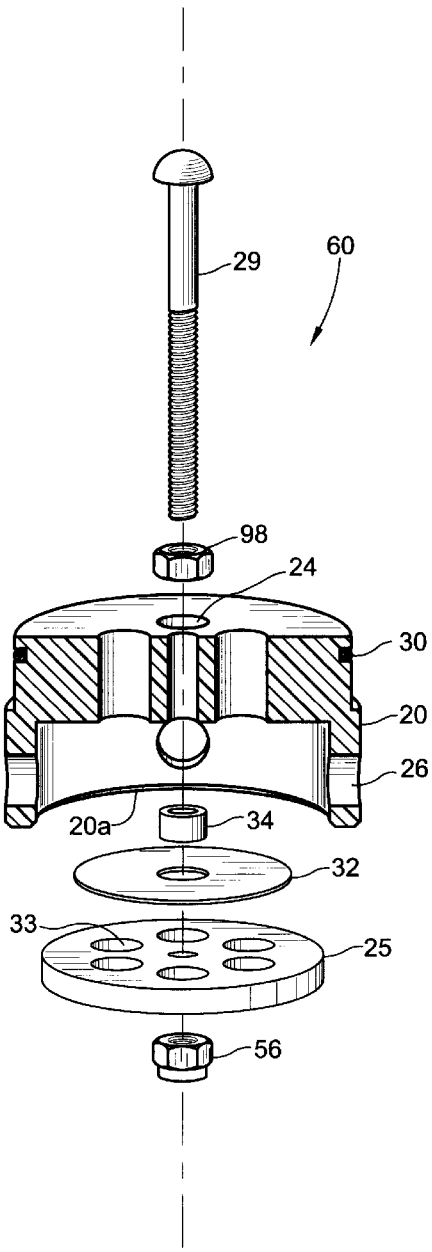
FIG. 10 is an isometric and partial sectional exploded view of the base assembly, taken generally along line 10—10 in FIG. 9.

Float assembly 18, as shown in FIG. 6, comprises a buoyant float body 72, upper and lower float end guides 27, commercial threaded rod 58 and commercial nuts 50 and 100. Water flow channels 23 are disposed opposite to each other on the perimeter of float body 72 and extend longitudinally through float body 72 and both float end guides 27, as seen in FIGS. 2A and 7.

Figure 12:
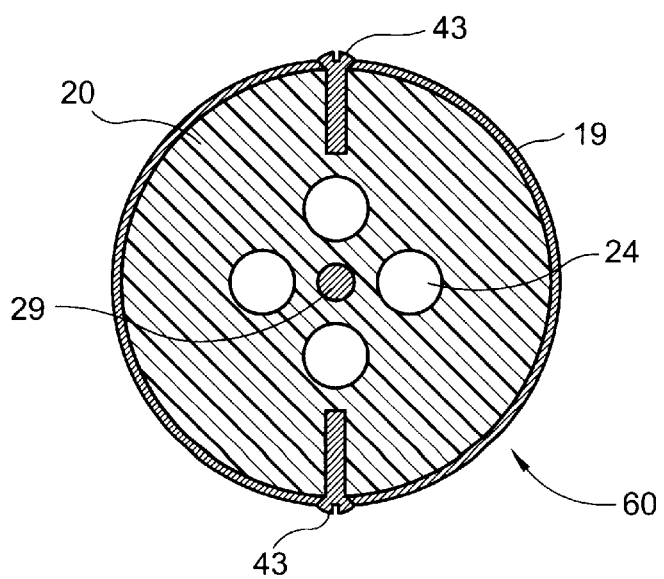
FIG. 12 is a sectional view of the base assembly, taken along line 12—12 in FIG. 5A, of the soil permeameter.

Base assembly 60, as shown in FIGS. 2B, 5A, 5B, 9, and 10, comprises bottom stopper 20 which provides a rigid mounting body for o-ring 30 which is in sealing contact with housing 19, commercial bolt 29, check valve 32, check valve guide 34, baffle 25, longitudinally disposed holes 24 through stopper 20, laterally disposed holes 26 in the skirt of bottom stopper 20, and commercial nuts 56 and 98. Check valve 32 moves freely in a vertical direction on check valve guide 34. Bottom stopper 20 is secured to housing 19 by commercial machine screws 43, as shown in FIGS. 2A, 11, and 12.

Figure 5A:
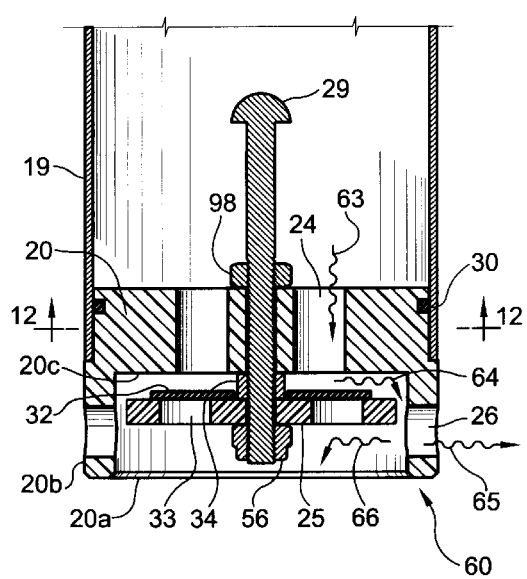
FIG. 5A is a sectional view of the lower part of the soil permeameter showing the base assembly and its check valve in its fully opened position, with flow arrows indicating the flow of water from the interior of the cylinder into the borehole.
Figure 5B:
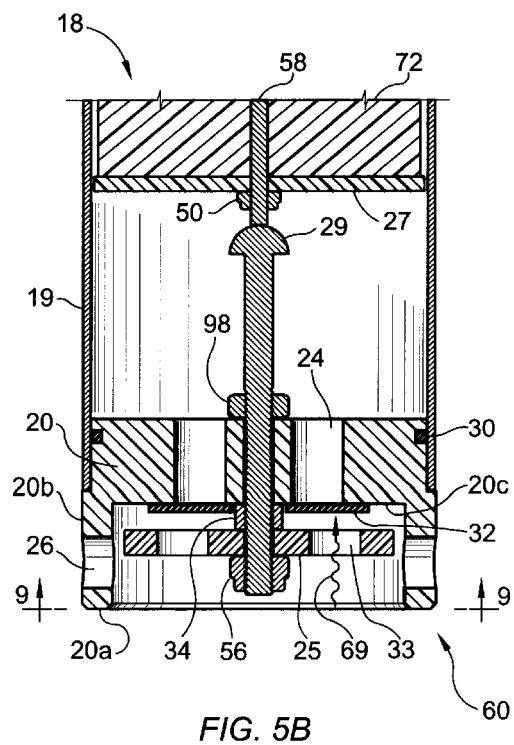
FIG. 5B is a sectional view of the lower part of the soil permeameter, showing the base assembly and its check valve in its fully closed position and with the buoyant float body in a lowered position, in contact with a bolt attached to the base assembly, as a flow arrow indicates attempted movement of water from the borehole toward the interior of the cylinder.

Check valve 32 rests on baffle 25 and remains open during normal operation, as illustrated in FIG. 5A, when water is flowing through base assembly 60 to borehole 11. However, check valve 32 rises into contact with countersunk bottom surface 20c and closes holes 24 to prevent backflow, as seen in FIG. 5B, if forced upward by reverse water flow, shown by flow arrow 69 through hole 33 in baffle 25.

Valve control assembly 17 and float assembly 18 provide flow control of water from reservoir 15 to maintain a constant head of water in borehole 11. The constant head of water is established by the preset level of the permeameter within borehole 11 and the resultant equilibrium of the pressure head induced by the height of water 70 in reservoir 15 and the rate of water absorption 47 into earthen material 11a, as depicted in FIG. 1. The force provided by any float assembly to effectively stop or throttle the flow at a valve must be sufficient to exceed hydrostatic pressures produced by the height of water 70 through hose column 14 and resultant pressure of water flow at control valve components 44 and 45 in the constant-head soil permeameter.

As the depth of testing increases, the increasing hydrostatic pressure at control valve components 44 and 45 of valve control assembly 17 requires progressively greater water displacement by float assembly 18 to throttle and maintain flow equilibrium. Other constant head devices utilizing a float alone with a float displacement equivalent to displacement of float assembly 18 become fully submerged and, therefore, ineffective at deep depths. In addition, the float assemblies of other constant head devices, not having a mechanical advantage means, displace a greater volume of water than the present invention at any given depth while maintaining equilibrium, thereby causing a correspondingly greater transient rise of the water level, H, within the borehole. This complicates determining the constant height of water for permeability test determinations.

The entire constant-head soil permeameter of this invention is constructed of stainless steel except for: a) o-rings 30, check valve 32, and valve seat 45 which are made of neoprene; b) top stopper 16, bottom stopper 20, baffle 25, and upper and lower float end guides 27 which are made of polycarbonate plastic; and c) float 72 which is made of a closed-cell foamed plastic.

Explanation of Forces Exerted within Valve Control Assembly 17

Figure 4C:
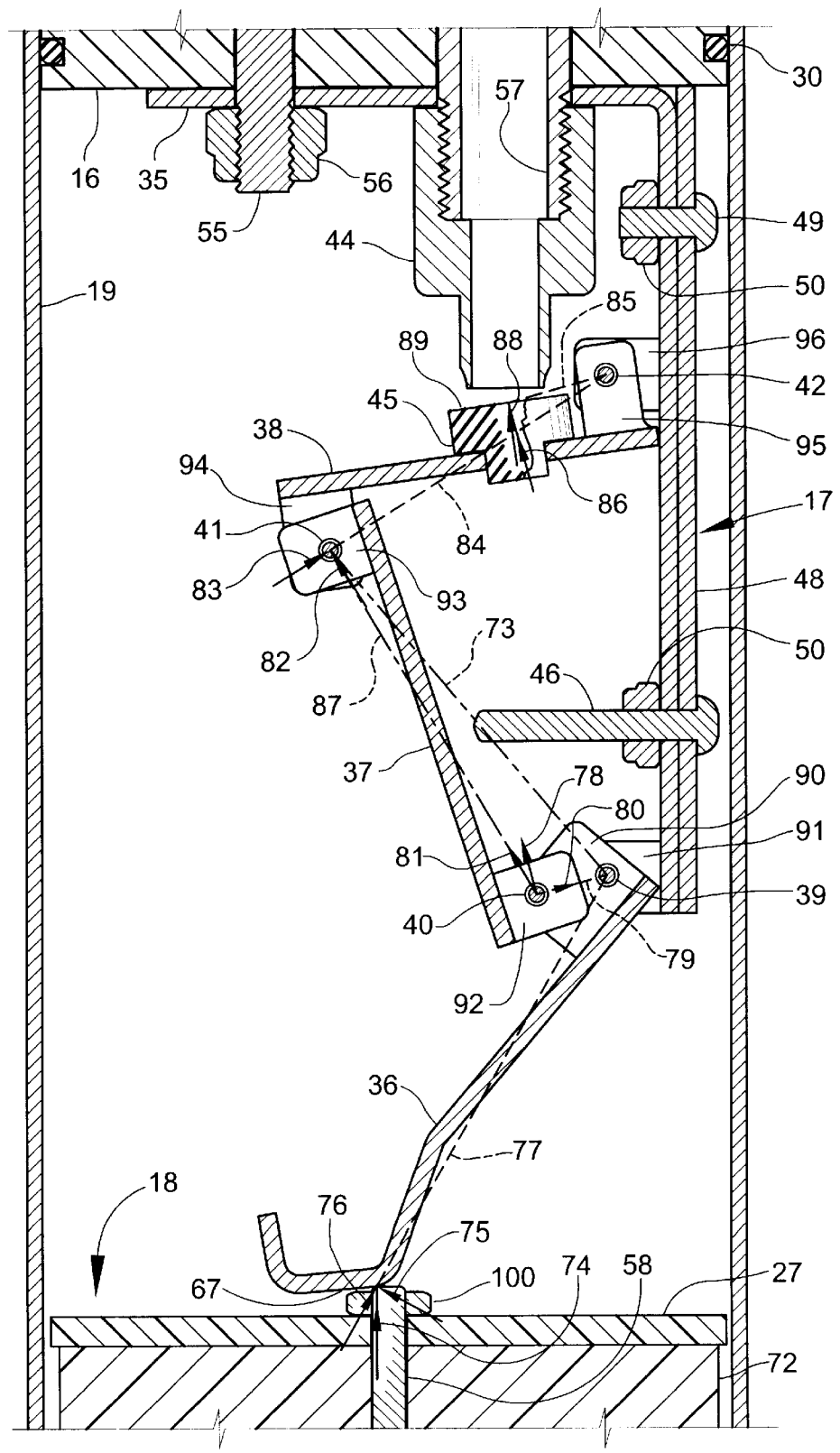
FIG. 4C is an enlarged sectional view of the middle part of the constant-head soil permeameter showing the valve control assembly in its fully opened position, with the force components acting at their respective pivots and the imaginary lines of action connecting the pivots.
Figure 4D:
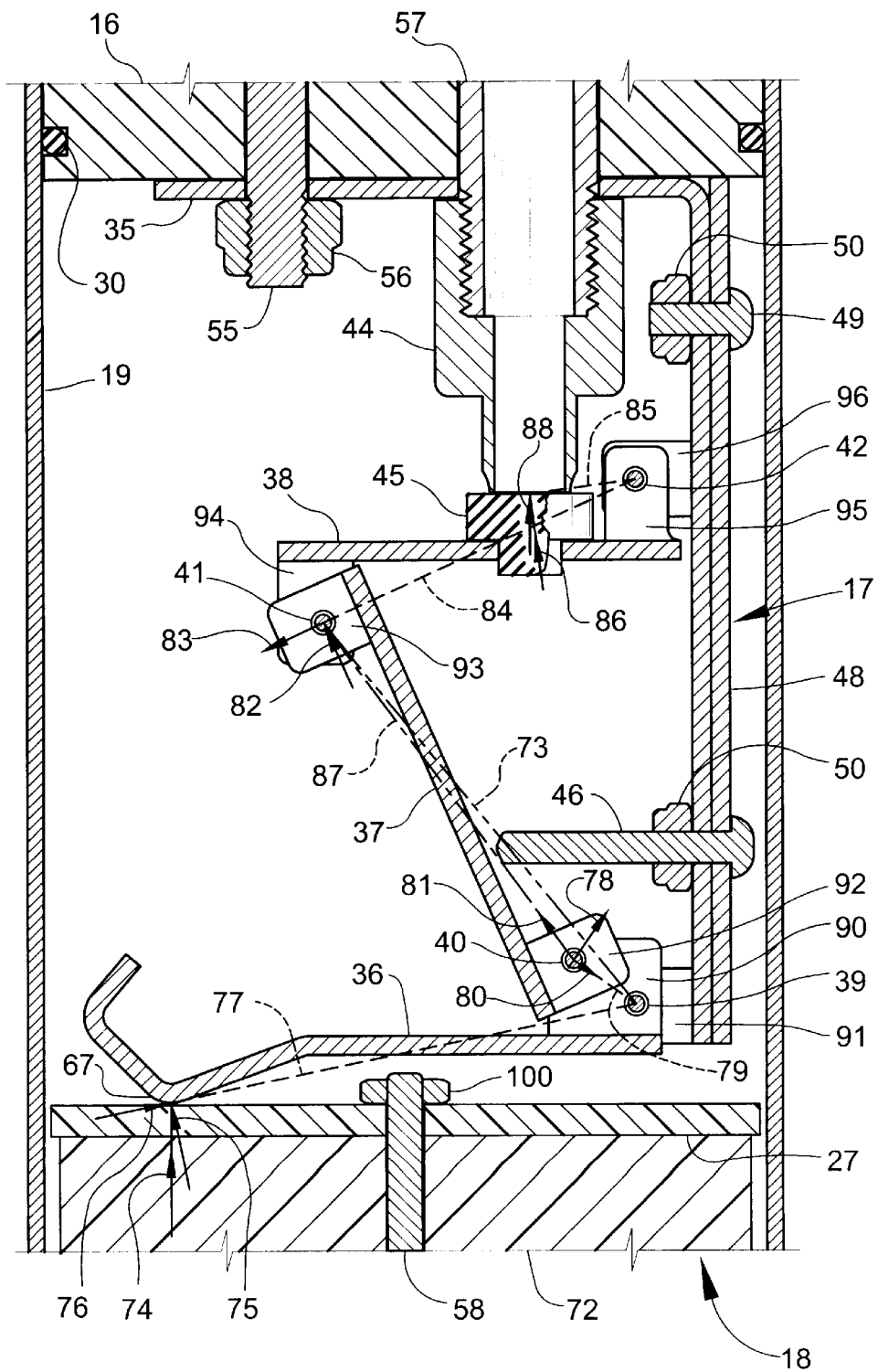
FIG. 4D is an enlarged sectional view of the middle part of the soil permeameter showing the valve control assembly in its fully closed position, with the force components and the imaginary lines of action in their changed positions.

The mechanical advantage ratio that is necessary for hydraulic testing at considerable depths is provided by the lever and link action of valve control assembly 17. A force along a line of action is required to make any body rotate about an axis. The perpendicular distance from the line of action of the force to the axis of rotation is the moment arm of the force and the product of the force and the moment arm of the force is the torque. As seen in FIGS. 4C and 4D, buoyant force 74, which has a line of action parallel to the longitudinal axis of valve support bracket 35, can be resolved into force components 75 and 76, which are, respectively, perpendicular and parallel to imaginary line 77 which joins the point of application of force 74 to the axis of actuating lever arm 36. Line 77 is, therefore, a moment arm of force 75 about pivot 39. The torque applied at pivot 39 is equal to the product of force 75 and the length of moment arm 77. Force 76 is directed toward the axis at pivot 39 and does not cause rotation.

As actuating lever arm 36 rotates around pivot 39, every point on actuating lever arm 36, including pivot 40 on lug 90, sweeps out the same angle at any time. The torque produced at pivot 39 from force 75 results in force 78 at pivot 40, which acts in a line of action perpendicular to moment arm 79. Force 78 is proportional to the ratio of the length of moment arm 77 to the shorter length of moment arm 79, thereby greatly exceeding force 75. Force 78 can be resolved into force 81 and force 80 along moment arm 79.

Force 81 lies along line of action 87, which is an imaginary line connecting pivot 40 and pivot 41 of link 37, all parts of which act as a rigid plate. Force 80 is directed toward pivot 39 and does not cause rotation. Forces 81 and 80 can be determined by two-dimensional equilibrium equations. The maximum ratio of force 81 to force 78 is achieved just before pivot 40 and line of action 87 of force 81 move across line 73. Line of action 87, however, is prevented from crossing line 73 by bolt 46, which limits the rotational travel of link 37.

Force 81 can be resolved into force components 82 and 83 which are, respectively, perpendicular and parallel to imaginary line 84 which joins the point of application of force 81 at pivot 41 with pivot 42, which is the axis of rotation of valve retaining lever arm 38. All parts of valve retaining lever arm 38, similarly to link 37 and actuating lever arm 36, act as a rigid plate. Line 84 is, therefore, a moment arm of force 82 about the axis at pivot 42.

The torque applied at pivot 42 is equal to the product of force 82 and the length of moment arm 84. Force 83 is directed either toward or away from the axis at pivot 42, depending on the degree of closure of valve control assembly 17, and does not cause rotation in either case. Force component 82 is nearly superimposed on line of force 87, as seen in FIG. 4C, because this line of force is nearly perpendicular to moment arm 84 at the fully open position.

As valve retaining lever arm 38 rotates around pivot 42, every point on valve retaining lever arm 38, including valve seat 45, sweeps out the same angle at any time. Force 86 is perpendicular to moment arm 85 and is a result of the torque at pivot 42 acting at the length of moment arm 85. Force 86 is proportional to the ratio of the length of moment arm 84 to the shorter length of moment arm 85, thereby greatly exceeding force 82 which applies the initial torque. Force 86 can be resolved into component force 88 that is perpendicular to face 89 of valve seat 45 and another force (neither shown nor numbered) that is parallel thereto.

Figure 13:
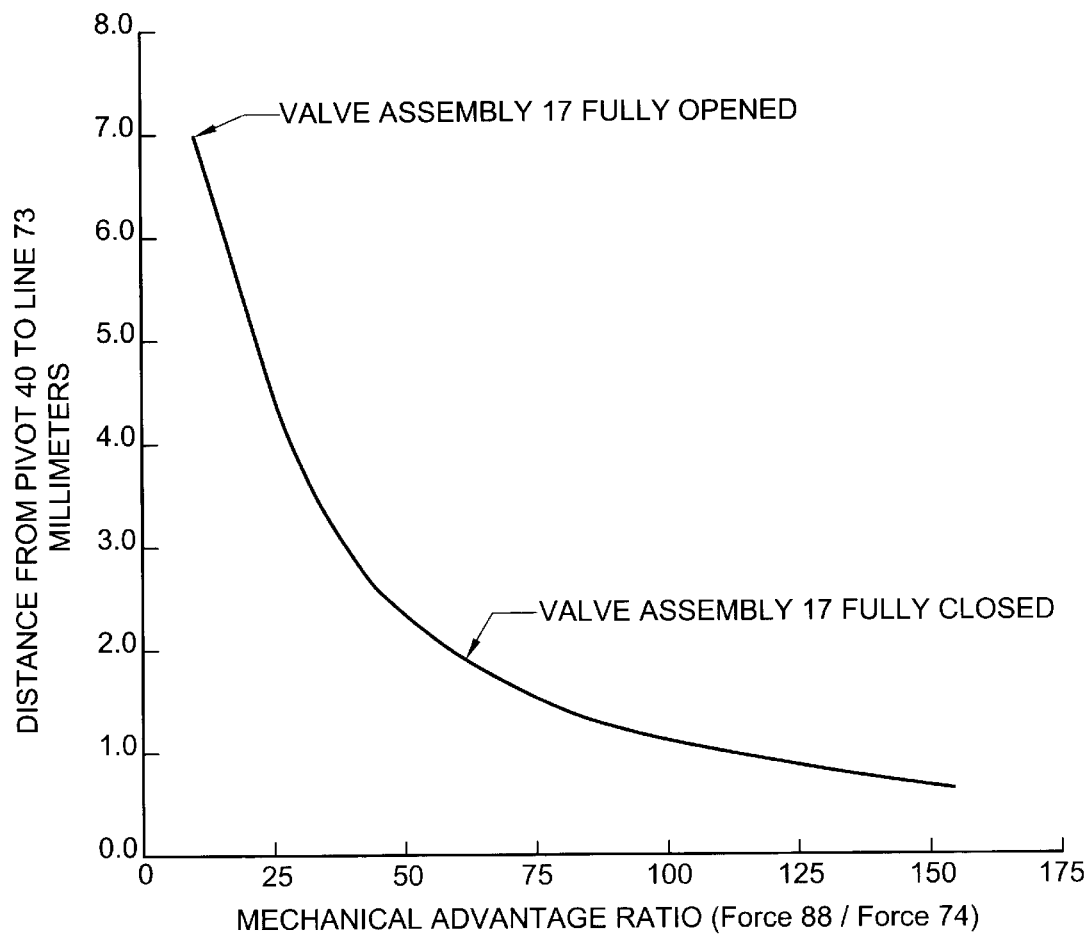
FIG. 13 is a chart of the mechanical advantage ratio, provided by the valve control assembly within the housing.

Force component 88 of force 86 has a line of action through the center of and perpendicular to face 89 of valve seat 45. Force 88, applied at the surface of valve seat 45, provides the force necessary to throttle or stop fluid flow from valve body 44. The mechanical advantage ratio of force 88 to buoyant force 74 ranges from approximately 10:1 at full valve opening (FIG. 4C) to approximately 60:1 at full valve closure (FIG. 4D). The mechanical advantage increases as a result of the cumulative mechanical advantages of actuating lever arm 36, link 37, and valve retaining lever arm 38. As can be seen in FIG. 13, the mechanical advantage ratio becomes larger at an increasing rate as pivot 40 and line of force 87 approaches, but does not cross, line 73.

Within the confines of housing 19, the distance between pivots 39 and 40 is the principal factor controlling amplification of the mechanical advantage ratio beyond 60:1. If the distance of 7.75 mm between pivots 39 and 40, as in the preferred embodiment herein described, is reduced, the torque about pivot 39 is increased in accordance with the ratio of the length of moment arm 77 to the length of moment arm 79, thereby correspondingly increasing resultant force 78. In addition, reduction in distance between pivots 39 and 40 simultaneously increases resultant force component 81 along line of action 87. However, this increased mechanical advantage and increased resultant force comes at a cost because the valve does not open as much as formerly and the maximum fluid flow is less.

The lugs and lever arms are quite rigid while using the preferred 14 gauge stainless steel materials, with a significant safety factor at a depth of even 40 meters. Consequently, the mechanical advantage ratio can be further increased, and the testing depth can thereby be significantly increased beyond 30 meters. The maximum depth of testing for the preferred embodiment described herein is limited to some undetermined depth greater than 40 meters because of limitations imposed by float capacity, fluid pressure, and turbulence created by the incoming water.

Valve control assembly 17 controls the water flow through the permeameter. At the beginning of a typical hydraulic conductivity test, water flows into hose connection 28 of valve control assembly 17 as shown by flow arrow 61 in FIG. 4A. Valve control assembly 17 is initially in a fully open position, thereby allowing water flow through valve body 44 and through the opening between valve body 44 and valve seat 45 as shown by flow arrow 62 in FIG. 4A.

This water falls on upper float end guide 27 and passes through water flow channels 23 of float assembly 18 and holes 24 of base assembly 60 and continues to flow beneath bottom stopper 20 and into borehole 11, as indicated by flow arrows 64, 65, 66 and as seen in FIG. 5A.

The water rises at equal corresponding levels in borehole 11 and inside housing 19. As the water level continues to rise, nut 100 of float assembly 18 strikes heel 67 of actuating lever arm 36, which is pivotally connected to valve support bracket 35 at pivot 39, and initiates upward rotation of actuating lever arm 36 around pivot 39. As float assembly 18 continues to rise, forcible contact at heel 67 of actuating lever arm 36 is transferred from nut 50 to float end guide 27, which maintains continuous sliding contact until partial or full valve closure is attained, as seen in FIGS. 1, 2A, and 4B.

As actuating lever arm 36 rotates upwardly around pivot 39, link 37, which is pivotally connected to pivot 40, revolves around pivot 40 and transfers the buoyant force provided by float assembly 18 to pivot 41 of valve seat retaining lever arm 38. This arm 38 is pivotally connected to valve support bracket 35 at pivot 42. It consequently revolves upwardly and progressively closes the opening between valve body 44 and valve seat 45. The mechanical advantage imparted by actuating lever arm 36, link 37, and valve seat retaining lever arm 38 increases with progressive valve closure.

Line 73 is an imaginary straight line passing through the centers of pivot 39 and pivot 41, as depicted in FIG. 4C. As float assembly 18 rises, heel 67 of actuating lever arm 36 slides from nut 100 onto upper float end guide 27 and continues to slide across guide 27 as actuating lever arm 36 revolves upwardly around pivot 39, thereby moving pivot 40 and link 37 toward line 73. The maximum mechanical advantage is attained just before pivot 40 reaches line 73. Pivot 40, however, is prevented from crossing line 73 by bolt 46, which limits the travel of link 37. The present invention provides a mechanical advantage ratio of approximately 60:1 at full valve closure.

Float assembly 18 provides the buoyant force required by valve control assembly 17 to throttle water flowing through channel 97 in hose connection 28, pipe 57, and valve body 44. Float assembly 18 moves freely inside housing 19 and is maintained in alignment by both float end guides 27, as shown in FIGS. 4A, 4B, 6, and 7. The upward travel range of float assembly 18 is limited by contact with valve control assembly 17 and the downward travel range is limited by contact with bolt 29. Prior to application of water during the hydraulic conductivity test, threaded rod 58 of float assembly 18 is at rest on bolt 29, as shown in FIG. 5B.

Water added to reservoir 15 during a typical test flows freely around float assembly 18 through flow channels 23 that are disposed longitudinally on float body 72 and float end guides 27, as well as in the annular space between float body 72 and housing 19, as shown in FIG. 7. Bolt 29, which limits downward travel of float assembly 18, prevents float assembly 18 from resting on the upper surface of bottom stopper 20, thereby allowing water applied during the test to flow freely through holes 24, as illustrated in FIGS. 5A and 12 by flow arrows 63, 64, 65, and 66, through bottom stopper 20 and also allowing the water to contact the entire lower surface of float assembly 18 when the water is rising inside housing 19.

Float assembly 18 rises with the rising water and displaces a volume of water equal in weight to the weight of float assembly 18. Float assembly 18 continues to rise in response to the rising water level and strikes heel 67 of actuating lever arm 36 and initiates upward rotation of actuating lever arm 36 around pivot pin 39, as illustrated in FIG. 4A. As float assembly 18 continues to rise, contact at heel 67 of actuating lever arm 36 is transferred to upper float end guide 27, which maintains continuous sliding contact until valve throttling control or full valve closure is attained, as seen in FIG. 4B. Float assembly 18 becomes partially submerged in proportion to the buoyant force required to throttle water flow from the contact orifice of valve body 44 by valve seat 45.

As float assembly 18 rises initially, valve seat 45 almost contacts valve body 44 to close channel 97 and stop the flow of water from reservoir 15; then valve seat 45 lowers slightly to establish an equilibrium fluid level in borehole 11 with only a slight fluctuation.

It is desirable to prevent inadvertent backflow entry of water, which may contain suspended soil particles or other debris, into the permeameter. Potential for reverse water flow, as shown by flow arrow 69 in FIG. 5B, may occur if the permeameter is placed in a borehole already containing water, if the borehole is advanced further after initial testing and water is not removed, or if the sidewall of the borehole collapses during the test and displaces a sufficient volume of water to cause backflow. Check valve 32 remains closed by pressure differential as long as the water level remains higher in the borehole than in the chamber of housing 19.

During normal operation, water flows through holes 24 in base assembly 60, as shown by flow arrow 63 in FIGS. 2B and 5A, then into the space above check valve 32 and around the annulus between baffle 25 and bottom stopper 20, as shown by flow arrow 64. Water continues to flow through lateral holes 26 of base assembly 60 into the annulus between housing 19 and borehole 11, as shown by flow arrow 65, and into the cavity below baffle 25 as shown by flow arrow 66 in FIG. 5A.

Baffle 25 and check valve 32 physically block direct entry of loose soil and other debris into the chamber of housing 19 when the permeameter of the invention is initially placed in the borehole. Bottom stopper 20 also incorporates o-ring 30 to provide a seal between bottom stopper 20 and housing 19, thereby further preventing entry of suspended soil particles and debris. Bottom stopper 20 is countersunk at its bottom 20c to leave a narrow circular rim 20b having a bottom edge 20a, as shown in FIG. 2B, thereby minimizing the contact area with borehole bottom 11b and providing negligible smearing or blockage of the absorptive soil surface at the bottom of the borehole.

During field operations to determine hydraulic conductivity, an unlined borehole 11 is drilled into the earth to a desired test depth with a suitable drilling or digging device to remove earthen materials and provide an approximately level surface at the bottom of the borehole. The constant-head soil permeameter of the invention is then lowered in a vertical position by cable 12 to rest upon bottom 11b of borehole 11, as shown in FIG. 1. Water is poured into reservoir 15 and flows by gravity through hose 14 and bore 97 in hose connection 28 into valve control assembly 17, as shown by flow arrow 61 in FIG. 4A. Valve control assembly 17 is initially in a fully open position, thereby allowing water to flow, as shown by flow arrow 62, through the opening between valve body 44 and valve seat 45.

Water then flows onto and around float assembly 18 through channels 23, as seen in FIGS. 2A and 7, into the annular space between float assembly 18 and housing 19, and into the lower part of housing 19. Water next flows through holes 24 in bottom stopper 20, as shown by flow arrow 63 in FIGS. 2B and 5A. During normal test procedures, check valve 32 is in its open position which allows water to flow freely through holes 24 in bottom stopper 20 into the space above check valve 32 and around the annulus between baffle 25 and bottom stopper 20, as shown by flow arrows 63 and 64 in FIG. 5A. Water then continues to flow through lateral holes 26 in skirt 20b into the annulus between the housing 19 and the perimeter of borehole 11, as shown by flow arrow 65 and into the cavity below baffle 25 as shown by flow arrow 66.

Filter vent assembly 21 allows exhausting of air as water rises inside the chamber within housing 19 and maintains atmospheric pressure equally inside and outside of housing 19 within borehole 11 at all times; this pressure equalization between level 22 within housing 19 and height of water H within borehole 11 is essential for maintaining equal water levels inside and outside of housing 19. Filter screen 31 of filter vent assembly 21 also stops entry of loose soil particles into housing 19.

Water rises freely at equal levels within the constant head permeameter and in the annular space between cylindrical housing 19 and the borehole sides until float assembly 18, which is buoyed by the rising water, engages valve control assembly 17. Water flow through valve body 44 of valve control assembly 17 is progressively throttled by valve seat 45 as float assembly 18 continues to rise until water level 22, as seen in FIG. 1, is approximately attained. After a suitable period of time that may vary from several minutes to one-half hour or more depending on soil characteristics, while water from borehole 11 is being transported radially into the surrounding soil matrix 11a, as shown approximately by permeation arrows 47, equilibrium water levels H and 22, which are equal, are attained.

The wetting-front continues to develop radially from borehole 11 as water levels H and 22 are maintained above the bottom of borehole 11 during the testing period. Water moves radially from the borehole through interparticle pores and along voids and fissures that are unique to any particular borehole in response to pressure induced by the constant head of water H, gravitational forces, and capillary forces within the earthen materials. The saturation that occurs within the wetting front during the test period is sometimes referred to as field saturation because some of the voids and pores may contain entrapped air and thereby reduce the potential flow that may occur under fully saturated conditions below the water table. An approximate steady state flow is attained in soil matrix 11a after a period of initial saturation and equilibrium is developed. Water level H is the resultant equilibrium level maintained by the permeameter of the invention in response to water absorption by soil and a pressure head of water level 70 in reservoir 15, as illustrated in FIG. 1. Once equilibrium of flow is approximately attained, reservoir 15 is filled approximately to the initial level 70 in preparation for recording test data.

After initial flow equilibrium is attained, the steady state flow of water absorbed by the soil is determined by recording at discrete time intervals the dropping water levels observed at graduations on reservoir 15. The optimum recording interval varies with the soil type and permeability and is determined by the user. For example, the optimum recording interval for highly permeable sandy soils may be approximately 5 minutes, but for slowly permeable clayey soils may be one-half hour or more. The total time during which observations are recorded may typically vary from on-half hour to 2 hours or more. The flow rate is derived from observations recorded during the selected time period. Level H of water in the borehole may be determined from direct observations or by the use of FIG. 14, which determines level 22 as a function of water flow rate and depth of the permeameter below ground surface 101. The estimated hydraulic conductivity is determined by factoring the steady state flow rate, water depth, and borehole geometry into an appropriate analytical solution.

Solution to Hydraulic Conductivity Values

Figure 14:
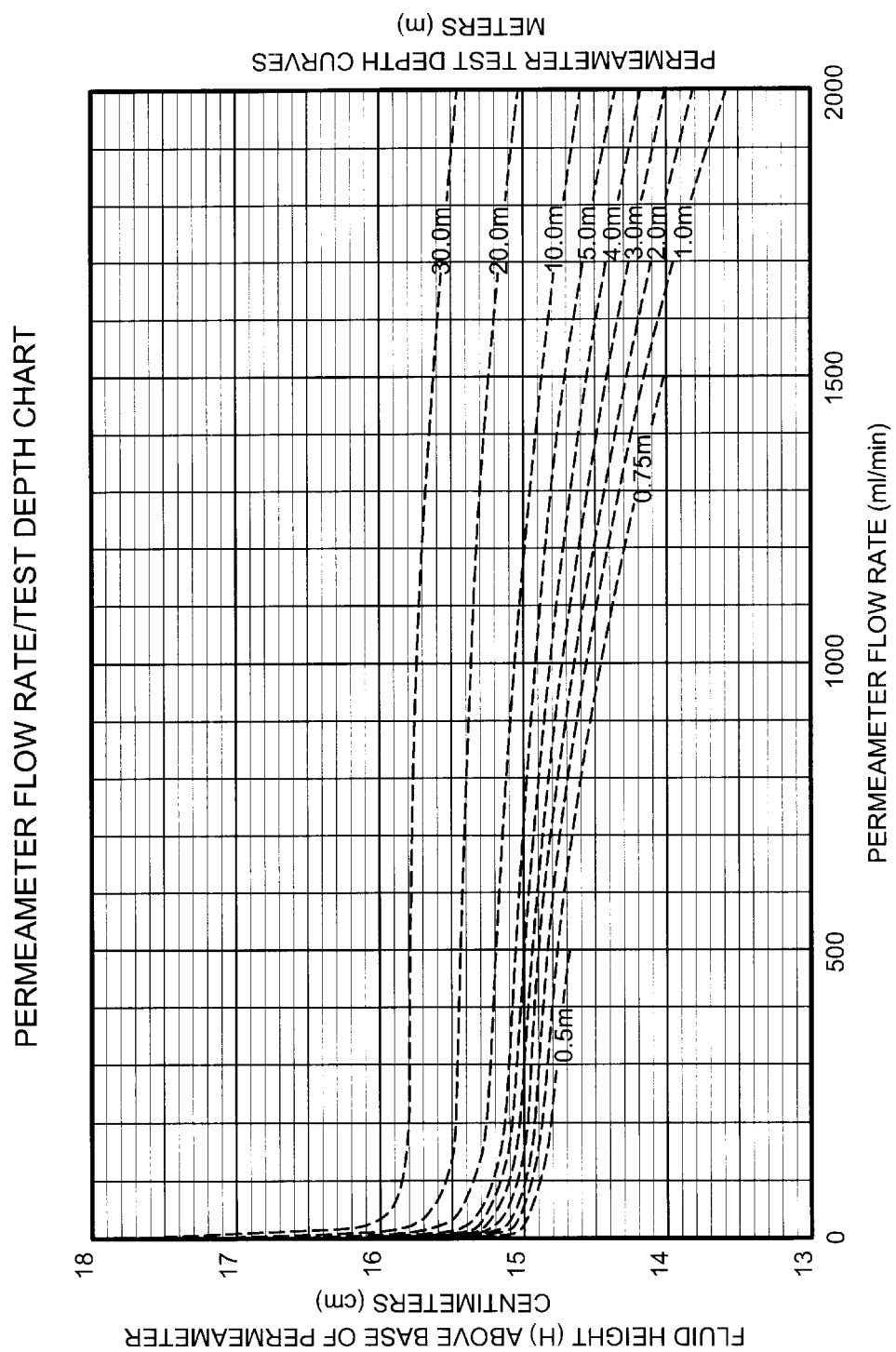
FIG. 14 is a chart containing permeameter test depth curves for the constant-head soil permeameter of the invention undergoing permeameter flow rates from zero to 2,000 ml/min.

The depth of water, indicated as level H in the borehole, may be determined from direct observations by use of a measuring tape or may be estimated by use of the Flow Volume/Test Depth Chart in FIG. 14. Test depth curves for placement of the permeameter below ground surface 101 range from 0.5 to 30.0 meters, as shown in FIG. 14. The test depth curves of FIG. 14 represent the mean of all observations, 95% of which are within +/−0.5 cm as determined by using an embodiment of the present invention. The test depth curves denote the height of water in the borehole if the permeameter rests on the bottom of the borehole. Alternatively, the permeameter can be suspended at any desired distance above the bottom of the borehole, and the suspended distance beneath rim 20a can be added to the height determined in FIG. 14 to obtain H.

The chart in FIG. 14 can be used to estimate the depth of water within the borehole at any flow rate of the invention ranging from zero to 2000 ml/min. For example, if the permeameter is placed on the bottom of the borehole, the depth of the borehole is 10.0 meters, and the flow rate is 500 mL/mm., then the estimated depth of the static water level H is approximately 15.2 cm. Where test depths are intermediate to the depth curves of FIG. 14, an appropriate interpolation is made.

The estimated hydraulic conductivity is determined by factoring the steady state flow rate of water into the soil, height of water within the borehole, and borehole geometry into an appropriate analytical solution. One example of an analytical solution has been developed by R. E. Glover (Zangar, 1953). This equation, suggested by Amoozegar and Warrick (1986) for use where the distance between the bottom of the borehole and an impermeable layer is at least twice as large as H, is:

$$K_S = Q[\sin h^{-1}(H/r) - (r^2/H^2+1)^{0.5} + r/H]/(2\pi H^2) \qquad \text{[Equation 1]}$$

Where $K_S$ = Saturated hydraulic conductivity,

Q = Steady-state flow rate of water into the soil,

H = Constant height of water in a cylindrical borehole, indicated as level H, and r = Radius of the cylindrical borehole.

Use of this equation is illustrated in the two following examples.

EXAMPLE 1

A cylindrical borehole 11 with diameter of 9.5 cm is augured to a depth of 0.6 meter. It is desired to establish a minimum height H of water equalling 25 cm above the bottom of the borehole, so that the permeameter is suspended 10 cm above the bottom of the borehole. During the test, in which volumetric readings of falling water levels in reservoir 15 are recorded at discrete time intervals spanning a two-hour period, it is determined that the steady-state flow rate of water Q into soil 11a is 5 ml/min. The constant height H of water is, therefore, 25.1 cm (15.1 cm from FIG. 14, plus 10 cm of suspended height). The radius r of borehole 11 is 4.75 cm, and the saturated hydraulic conductivity, $K_S$, from Equation 1 is $3.2 \times 10^{-5}$ cm/sec. This is a low hydraulic conductivity value, typical of silt and clay soils.

EXAMPLE 2

A circular borehole 11 with diameter of 9.5 cm is augured to a depth of 10.0 meters. It is desired to establish a minimum height H of water equalling 25 cm above the bottom of the borehole and to suspend the permeameter at a height of 10 cm above the bottom of the borehole. During a test period of one-half hour, it is determined that the steady-state flow rate of water Q into soil 11a is 900 ml/min. The constant height H of water is, therefore, 25.1 cm (15.1 cm from FIG. 14, plus 10 cm of suspended height). The radius r of the borehole is 4.75 cm and the saturated hydraulic conductivity from Equation 1 is $5.8 \times 10^{-3}$ cm/sec. This is a high hydraulic conductivity value, typical of sandy soils.

In the event that water covers bottom 11b of borehole 11 at the time of inserting the permeameter in borehole 11, check valve 32 of base assembly 60 closes and stops water and suspended soil particles from entering housing 19, as seen in FIG. 5B. It is desirable to prevent inadvertent entry of water, which may contain suspended soil particles or other debris, into the permeameter.

This situation may occur if seepage water enters the borehole after it is drilled or if the borehole is advanced to a deeper depth after an initial test has been performed and the remaining water has not been removed during drilling or has not drained completely away into the soil. Water must be removed from the borehole if the initial water levels exceed the equilibrium height of the permeameter. If the water level is a result of seepage or groundwater inflow, the test procedure is invalid because the permeameter is designed to measure hydraulic conductivity as a result of outflow to the soil. Potential reverse water flow may also occur if the sidewall of the borehole collapses during the test and displaces a sufficient volume of water to cause backflow.

Because it will be readily apparent to those skilled in the constant-head soil permeameter art that innumerable variations, modifications, applications, and extensions of the principles hereinbefore set forth can be made without departing from the spirit and the scope of the invention, what is hereby defined as such scope and is desired to be protected should be measured, and the invention should be limited, only by the following claims.

What is claimed is:

1. A constant-head soil permeameter comprising a tubular cylinder having a top end, a bottom end, means for introducing a liquid into said top end, means for selectively closing said bottom end, and means for preventing falling debris from entering said top end while enabling air to flow into and out of said cylinder, said top end and said bottom end being defined in relation to usage within a vertically disposed borehole in materials permeable to said liquid, wherein:
   A) said cylinder contains a valve having a valve control assembly that provides a mechanical advantage ratio for shutting off said introducing of liquid;
   B) said liquid is water, said permeable materials are earthen, and said borehole has a bottom disposed above a water table in said earthen materials; and
   C) said mechanical advantage ratio ranges from approximately 10:1 at full valve opening to approximately 60:1 at full valve closure.

2. The constant-head soil permeameter of claim 1, wherein said valve control assembly comprises a compound lever and link assembly.

3. The constant-head soil permeameter of claim 2, wherein said compound lever and link assembly comprises:
   A) a valve support bracket which is longitudinally disposed and rigidly supported within said cylinder;
   B) an actuating lever arm, having two ends, which is attached at one end to a first pivot which is attached to said valve support bracket;
   C) a link, having two ends, which is attached at one end to a second pivot which is attached to but spaced apart by a selected distance from said first pivot; and
   D) a valve seat retaining lever arm, having two ends, which is pivotally attached at one end to said valve support bracket and is pivotally attached at its other end to a pivot attached to the other end of said link.

4. The constant-head soil permeameter of claim 3, wherein:
   A) said top end of said cylinder comprises a top stopper having an upper side and a lower side; and
   B) said means for introducing said water into said top end comprises a reservoir for containing said water, a hose connection which is rigidly attached to said upper side and has a bore therewithin, a hose for connecting said reservoir to said hose connection, and a valve body which is rigidly attached to said lower side and has a bore therewithin in fluid communication with said bore within said hose connection.

5. The constant-head soil permeameter of claim 4, wherein said valve seat retaining lever arm comprises a valve seat which is attached thereto in facing relationship to said valve body and is adapted for selectively shutting off said introducing of water.

6. The constant-head soil permeameter of claim 5, wherein said cylinder additionally contains a buoyant float body that is axially movable within said cylinder and has upper and lower surfaces.

7. The constant-head soil permeameter of claim 6, wherein said upper surface of said buoyant float body exerts pressure against said other end of said actuating lever arm when said float is supported by water within said cylinder.

8. The constant-head soil permeameter of claim 1, wherein said means for preventing falling debris and soil from entering said top end while enabling air flow into and out of said cylinder comprises an inverted J-shaped tube, having a long portion which passes through said top stopper and a short portion having a filter screen at the outer end thereof, said filter screen being disposed to face toward said upper side of said top stopper and being spaced from said upper side.

9. The constant-head soil permeameter of claim 1, wherein said means for selectively closing said bottom end comprises:
   A) a bottom stopper, having an upper surface and a lower surface, which is rigidly attached to said cylinder;
   B) an o-ring encircling said bottom stopper and in sealing contact with said cylinder;
   C) an axially disposed bolt attached to said bottom stopper and extending upwardly beyond said upper surface;
   D) at least one longitudinally disposed hole extending through said stopper; and
   E) a check valve disposed beneath said lower surface, whereby reverse flow of said water from said borehole toward said bottom stopper lifts said check valve and closes said at least one hole and said bottom end.

10. The constant-head soil permeameter of claim 2, wherein the effective testing depth range is from 15 centimeters to at least 30 meters.

11. The constant-head soil permeameter of claim 2, wherein the permeability testing range is from about $10^{-6}$ centimeters/second to about $10^{-2}$ centimeters/second.

12. The constant-head soil permeameter of claim 2, wherein the range of water flow through said permeameter is from zero to at least 2000 milliliters/minute.

13. A constant-head soil permeameter for measuring hydraulic conductivity in earthen materials having a water table, said permeameter being effective, when disposed in a borehole within said earthen materials, at depths above said water table from about 15 centimeters to at least about 30 meters, and comprising:
  A) means for introducing water into said permeameter and then into said borehole, comprising a valve body through which said water is introduced;
  B) a float assembly, disposed within said permeameter, providing a buoyant force for closing a bore within said valve body; and
  C) a water flow control valve having a lever-and-link valve control assembly that increases said buoyant force by a factor ranging from about 10:1 at fully open valve position to at least about 60:1 at full closure thereof.

14. The constant-head soil permeameter of claim 13 that has a permeability testing range varying from about $10^{-6}$ centimeters per second to about $10^{-2}$ centimeters per second.

15. The constant-head soil permeameter of claim 13 which comprises a closed cylinder and wherein said lever-and-link valve control assembly comprises:
  A) a valve support bracket which is longitudinally disposed and rigidly supported within said cylinder, adjacent to the inner side thereof, said cylinder having a top end and a bottom end when disposed in said borehole;
  B) an actuating lever arm, having a free end resting on said float assembly to receive said buoyant force and a pivot end which is attached to a first pivot which is attached to said valve support bracket;
  C) a link, having lower and upper ends, which is attached at said lower end to a second pivot which is attached to but spaced apart by a selected distance from said first pivot; and
  D) a valve seat retaining lever arm, having two ends, which is pivotally attached at one end to said valve support bracket and is pivotally attached at its other end to a pivot attached to said upper end of said link, each said pivot being mounted on a pair of spaced-apart lugs and comprising a pivot pin inserted into a hole which is disposed perpendicularly to said lugs.

16. The constant-head soil permeameter of claim 15 wherein:

A) said valve support bracket has an upper pair and a lower pair of spaced-apart lugs attached perpendicularly thereto and projecting toward the center of said cylinder;
  B) said actuating lever arm has one pair of said spaced-apart lugs attached perpendicularly thereto at said pivot end and projecting upwardly, being attached to said lower pair by said first pivot;
  C) said link has two pairs of said spaced-apart lugs attached perpendicularly thereto at said upper and lower ends and projecting toward said valve support bracket, one said pair being attached by said second pivot to said one pair of spaced-apart lugs on said pivot end and being spaced from said first pivot by said selected distance; and
  D) said valve seat retaining lever arm has two pairs of said spaced-apart lugs attached perpendicularly thereto at said ends thereof and projecting in opposite directions, one pair being pivotally attached to said upper pair on said valve support bracket and the other pair being pivotally attached to said pair of spaced-apart lugs on said upper end of said link.

17. A constant-head soil permeameter, adapted for operational use within a borehole in earthen materials, said borehole having a bottom, comprising a cylindrical housing having a top end and a bottom end when within said borehole, said bottom end having a flow-through means for allowing water entering said top end to flow through said bottom end and to form a first water level therewithin and to flow into said borehole to form a second water level therewithin when said second water level is lower than said first water level and having a closing means for preventing water from flowing into said cylindrical housing when said second water level is higher than said first water level, wherein said flow-through means comprises a bottom stopper which is rigidly attached to said cylindrical housing, has a countersunk bottom surface forming a downwardly extending skirt that contacts said bottom of said borehole when said permeameter is resting thereupon, has at least one longitudinally disposed hole through said stopper, and has at least one laterally extending hole through said skirt.

18. The constant-head soil permeameter of claim 17, wherein said closing means comprises a check valve guide which is axially and rigidly attached to said countersunk bottom surface of said stopper, a disk-shaped check valve which is loosely and axially fitted to said check valve guide, and a disk-shaped baffle, having a plurality of longitudinally disposed holes therethrough, which is rigidly and perpendicularly attached to said check valve guide and disposed beneath said check valve, whereby backflow of said water from said borehole toward said bottom stopper passes through said plurality of holes in said baffle and lifts said check valve to block all said longitudinally disposed holes in said bottom stopper.

* * * * *